| United States Patent [19] | [11] Patent Number: 5,057,628 |
| Edwards et al. | [45] Date of Patent: *Oct. 15, 1991 |

[54] ALKOXYLATION PROCESS CATALYZED BY COMPOUNDS OF THE RARE EARTH ELEMENTS

[75] Inventors: Charles L. Edwards, Houston; Richard A. Kemp, Stafford, both of Tex.

[73] Assignee: Shell Oil Company, Houston, Tex.

[*] Notice: The portion of the term of this patent subsequent to Oct. 15, 2008 has been disclaimed.

[21] Appl. No.: 482,378

[22] Filed: Feb. 20, 1990

Related U.S. Application Data

[63] Continuation-in-part of Ser. No. 215,653, Jul. 6, 1988, abandoned, which is a continuation-in-part of Ser. No. 204,329, Jun. 9, 1988, abandoned, which is a continuation-in-part of Ser. No. 134,272, Dec. 17, 1987, abandoned.

[51] Int. Cl.$^5$ ............................................. C07C 41/03
[52] U.S. Cl. ..................................... 568/618; 568/620; 568/608; 568/45; 568/55; 568/679; 568/678; 260/410.6; 560/93; 560/209; 560/200; 560/105; 560/112; 560/240; 564/399; 564/475; 564/505; 530/230; 530/232; 530/217
[58] Field of Search ............... 568/618, 620, 608, 45, 568/55, 678, 679; 260/410.6; 560/93, 209, 200, 105, 112, 240; 564/399, 475, 505; 530/230, 232, 217

[56] References Cited

U.S. PATENT DOCUMENTS

| 4,528,364 | 7/1986 | Prier | 528/370 |
| 4,658,065 | 4/1987 | Aoshima et al. | 564/487 |
| 4,665,236 | 5/1987 | Edwards | 568/618 |

FOREIGN PATENT DOCUMENTS

250168 12/1987 European Pat. Off. .

OTHER PUBLICATIONS

Y. Zhang, Inorganica Chemica Acta, 155 (1989), 263–265.

*Primary Examiner*—Howard T. Mars
*Attorney, Agent, or Firm*—Pamela J. McCollough

[57] ABSTRACT

Alkylene oxide adducts of organic compounds having active hydrogen atoms are prepared by a process which comprises contacting and reacting an alkylene oxide reactant comprising one or more vicinal alkylene oxides with an active hydrogen containing reactant comprising one or more compounds having active hydrogen atoms in the presence of a catalytically effective amount of one or more compounds of one or more of the rare earth elements. The product alkoxylates are known to be useful, for instance, as nonionic surfactants, wetting and emulsifying agents, solvents, and chemical intermediates.

58 Claims, No Drawings

ALKOXYLATION PROCESS CATALYZED BY COMPOUNDS OF THE RARE EARTH ELEMENTS

This is a continuation-in-part of the application Ser. No. 07/215,653, filed July 6, 1988, the application Ser. No. 204,329, filed

BACKGROUND OF THE INVENTION

This invention relates to an alkoxylation process in which alkylene oxides are reacted with compounds having active hydrogen atoms in the presence of catalysts comprising one or more compounds of the rare earth elements. In particularly preferred embodiments, the invention relates to processes for the preparation of alkoxylate products useful as nonionic surfactants.

A large variety of products useful, for instance, as nonionic surfactants, wetting and emulsifying agents, solvents, and chemical intermediates, are prepared by the addition reaction (alkoxylation reaction) of alkylene oxides (epoxides) with orgahic compounds having one or more active hydrogen atoms. For example, particular mention may be made of the alkanol ethoxylates and alkyl-substituted phenol ethoxylates prepared by the reaction of ethylene oxide with aliphatic alcohols or substituted phenols of about 6 to 30 carbon atoms. Such ethoxylates, and to a lesser extent corresponding propoxylates and compounds containing mixed oxyethylene and oxypropylene groups, are widely employed as nonionic detergent components of commercial cleaning formulations for use in industry and in the home. As another example, the addition reaction of propylene oxide with polyols provides intermediates for the preparation of polyurethane products.

An illustration of the preparation of an alkanol ethoxylate (represented by formula III below) by addition of a number (n) of ethylene oxide molecules (formula II) to a single alkanol molecule (formula I) is presented by the equation

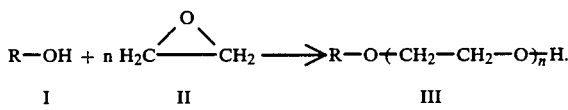

$$R\text{---}OH + n\ H_2C\overset{O}{\overset{\diagdown}{\text{---}}}CH_2 \longrightarrow R\text{---}O\text{-}(CH_2\text{---}CH_2\text{---}O)_{\overline{n}}H.$$

I   II   III

The present invention particularly relates to an alkoxylation reaction catalyzed by one or more compounds of one or more of the rare earth elements.

Conventional alkoxylation catalysts include the basic salts of the alkali metals of Group I of the Periodic Table, e.g., sodium, potassium, rubidium, and cesium, and the basic salts of certain of the alkaline earth metals of Group II of the Periodic Table, e.g., calcium, strontium, barium and in some cases magnesium. Conventional acidic alkoxylation catalysts include, broadly, the Lewis acid or Friedel-Crafts catalysts. Specific examples of these acid catalysts are the fluorides, chlorides, and bromides of boron, antimony, tungsten, iron, nickel, zinc, tin, aluminum, titanium and molybdenum. The use of complexes of such halides with, for example, alcohols, ethers, carboxylic acids, and amines has also been reported. Still other examples of known acidic alkoxylation catalysts are sulfuric and phosphoric acids., perchloric acid and the perchlorates of magnesium, calcium, manganese, nickel and zinc., certain metal oxalates, sulfates, phosphates, carboxylates and acetates; alkali metal fluoroborates; zinc titanate; and certain salts of benzene sulfonic acid. Other art on the subject of alkoxylation includes U.S. Pat. No. 4,727,199, which describes a process for reacting a liquid or solid alKylene oxide with a liquid or gaseous active hydrogen compound in the presence of a catalytic amount of an anion-bound metal oxide heterogenous catalyst, wherein the anion is $SO_4$, $BF_4$, $CO_3$, $BO_3$, $PO_4$, $SeO_4$, $MoO_4$, $B_4O_7$ or $PF_6$ and the metal oxide is an oxide of zirconium, nickel, aluminum, tin, calcium, magnesium, iron, titanium, thorium, hafnium, or rubidium. Still other prior art describes the use of zeolitic materials as alkoxylation catalysts, while European patent application 0250108 and other art cited therein disclose lamellar clay catalysts.

Alkylene oxide addition reactions are known to produce a product mixture of various alkoxylate molecules having different numbers of alkylene oxide adducts (oxyalkylene adducts) e.g., having different values for the adduct number n in formula III above. The adduct number is a factor which in many respects controls the properties of the alkoxylate molecule, and efforts are made to tailor the average adduct number of a product and/or the distribution of adduct numbers within a product to the product's intended service. In certain preferred embodiments, the present invention provides a process characterized by enhanced selectivity for the preparation of alkoxylate mixtures in which a relatively large proportion of the alkoxylate molecules have a number (n) of alkylene oxide adducts that is within a relatively narrow range of values.

It is known in the art that alcohol alkoxylate products having a narrow range alkylene oxide adduct distribution are preferred for use in certain detergent formulations (Great Britain Patent No. 1,462,134; Derwent Publications Research Disclosure number 194,010). Narrow-range alcohol alkoxylates are also known to be particularly valuable as chemical intermediates in the synthesis of certain carboxyalkylated alkyl polyethers (U.S. Pat. No. 4,098,818) and of certain alkyl ether sulfates (Great Britain Patent No. 1,553,561). Conventional commercial alkoxylate preparation, which has in large part been limited to the use of basic catalysts, particularly the metals sodium and potassium and their oxides and hydroxides, yields only a relatively broad distribution range product. Conventional acid-catalyzed alkoxylation reactions have long been known to produce a more narrow range product than that obtained with the alkali metal catalysts. However, acid catalysts have substantial disadvantage in several other respects. For instance, the acids are often unstable with limited life and effectiveness as catalysts in the alkoxylation mixture. Both the acid catalysts themselves and their decomposition products catalyze side reactions producing relatively large amounts of polyalkylene glycols, and also react directly with the components of the alkoxylation mixture to yield undesirable, and often unacceptable, by-products such as organic derivatives of the acids.

Also of substantial importance in alkoxylation processes is the ability of the process to minimize the quantity of unreacted (or residual) active hydrogen reactant remaining in the final product. A high level of residual reactant either represents a loss of valuable reactant, or requires that further processing of the product be carried out to recover the reactant. Moreover, the presence of the unreacted material is often of disadvantage from the standpoint of product quality and environmental concerns. For instance, residual alkanol in a detergent alcohol ethoxylate product contributes to volatile organic emissions during spray drying of detergent formulations.

It has recently been reported in the art that, in addition to conventional acidic catalysts, a number of other substances have been found to function as catalysts or in co-catalyst combinations which are capable of producing relatively narrow distributions for the oxyalkylene adducts of higher alkanols and other active hydrogen containing compounds. For instance, it has recently been disclosed (U.S. Pat. Nos. 4,306,093 and and No. 4,239,917, and published European Patent Applications 0026544, 0026546, 0026547 and that certain compounds of barium, strontium, and calcium promote narrow-range alkoxylation products. U.S. Pat. Nos. 4,210,764 and No. 4,223,164 describe the use of cresylic acids to promote alkoxylation catalyzed by barium and strontium compounds. U.S. Pat. No. 4,302,613 reports that a more peaked reaction product can be obtained by combining barium and strontium alkoxylation catalysts with co-catalysts such as calcium oxide, calcium carbide, calcium hydroxide, magnesium metal, magnesium hydroxide, zinc oxide and aluminum metal. U. S. Pat. No. 4,453,023 describes a process for preparing alkoxylates having a narrower molecular weight distribution which employs a catalyst comprising a barium compound and a promoter selected from the class consisting of superphosphoric acid, phosphoric acid, diphosphoric acid, triphosphoric acid, phosphorous acid, dihydrogen phosphate compounds, oxides of phosphorous, carbon dioxide, and oxalic acid. U.S. Pat. No. 4,453,022 describes a similar process wherein the catalyst comprises a calcium or strontium compound and a promoter selected from the class consisting of superphosphoric acid, phosphoric acid, diphosphoric acid, triphosphoric acid, phosphorous acid, dihydrogen phosphate compounds, oxides of phosphoru sulfuric acid, bisulfate compounds, carbonic acid, bicarbonate compounds, carbon dioxide, oxalic acid and oxalic acid salts, sulfur trioxide, sulfur dioxide, and sulfurous acid. Published PCT application WO 85/00365 discloses other activated calcium containing alkoxylation catalysts capable of producing narrow range alkoxylation products. U.S. Pat. No. 4,375,564 reports that a narrow range product results from alkoxylation reactions catalyzed by a magnesium compound in combination with a compound of one of the elements aluminum, boron, zinc, titanium, silicon, molybdenum, vanadium, gallium, germanium, yttrium, zirconium, niobium, cadmium, indium, tin, antimony, tungsten, hafnium, tantalum, thallium, lead and bismuth. U.S. Pat. No. 4,483,941 discloses catalysts for alkoxylation reactions which comprise either $BF_3$ or $SiF_4$ in combination with an alkyl or alkoxide compound of aluminum, gallium, indium, thallium, titanium, zirconium, and hafnium. U.S. Pat. No. 4,456,697 describes an alkoxylation catalyst which comprises a mixture of HF and one or more metal alkoxides. Japanese patent specification 52051307 to Tokuyama Soda KK discloses the selective preparation of mono- rather than di- or tri-alkylene glycol esters from alkylene oxide and alcohol using solid acid catalysts such as silica, alumina, titania, vanadium pentoxide, antimony pentoxide, titanyl sulfate, tungstic acid, phosphotungstic acid, and silver perchlorite.

Recently issued U.S. Pat. No. 4,721,816 claims a process for preparing narrow range distribution alkoxylates, wherein the catalyst is a combination of one or more sulfur-containing acids with one or more aluminum alcoholate or phenolate compounds. U.S. Pat. No. 4,721,817 claims a similar process wherein the combination contains one or more phosphorus-containing acids.

U.S. Pat. Nos. 4,665,236 and No. 4,689,435 describe a process for the alkoxylation of active hydrogen reactants using certain metal oxo alkoxide catalysts. With regard to the use in this invention of catalysts comprising one or more compounds of the rare earth elements, the catalysts described in these patents include compounds in which one of the metal species in the bimetallic molecule is a rare earth element.

The aforementioned European application 0250168 discloses lamellar clay catalysts which have been ion exchanged with rare earths.

SUMMARY OF THE INVENTION

It has now been found that compounds of the rare earth elements are effective catalysts for the addition reaction of alkylene oxides with organic compounds having active hydrogen atoms.

The present invention is particularly directed to a process for the preparation of alkoxylates of active hydrogen containing organic compounds which comprises contacting and reacting one or more vicinal alkylene oxide compounds with one or more active hydrogen containing organic compounds (e.g., alcohols, phenols, thiols, amines, polyols, carboxylic acids, etc.) having one or more active hydrogen atoms, in the presence of a catalyst comprising one or more of the rare earth elements.

As the terminology is used herein, the "rare earth" elements are those of atomic numbers 39, and 57 through 71; elements of the "lanthanum series" are those of atomic numbers 57 through 71; the "lanthanide" elements are those of atomic numbers 58 through 71. Traditionally, the lanthanum series has further been divided into the "cerium earth" group of atomic numbers 57 through 62, the "terbium earth" group of atomic numbers 63 through 66, and the "yttrium earth" group of atomic numbers 67 through 71 (so named not because yttrium is a member of the group, but because yttrium is found with these elements in nature).

In one preferred embodiment of the invention, the catalyst for the process of the invention comprises one or more simple metal, i.e., mono-metallic, salts of one or more of the rare earth metals. In another specific embodiment, the catalyst comprises one or more compounds of one or more of the lanthanum series elements. In a further embodiment, the catalyst comprises one or more compounds of one or more of the lanthanide elements. In another specific embodiment, the catalyst comprises one or more compounds of one or more elements of the cerium earth group. In still another specific embodiment, the catalyst comprises a mixture of rare earth metal salts or other compounds wherein the distribution of the rare earth elements substantially corresponds to that of a naturally occurring rare earth ore such as monazite, bastnasite, xenotime, gadolinite and euxenite.

Suitable catalyst compounds are either organic or inorganic and are either homogeneous or heterogeneous in the alkoxylation process mixture.

DESCRIPTION OF THE PREFERRED EMBODIMENTS

The present invention centers upon discoveries associated with the use in an alkoxylation process of a certain class of catalysts. Apart from the use of such catalysts, the process of the invention is, as a general rule, suitably conducted using such reactants and practicing under such processing procedures and reaction conditions as are well known to the art for alkoxylation reactions. Certain preferences may, however, be expressed for particular reactants, procedures and conditions.

Thus, for instance, the invention is preferably applied to processes utilizing alkylene oxide (epoxide) reactants selected from the group consisting of vicinal alkylene oxides, particularly the lower alkylene oxides and more particularly those in the $C_2$ to $C_4$ range. In general, the alkylene oxides are represented by the formula

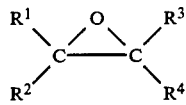

wherein each of the $R^1$, $R^2$, $R^3$ and $R^4$ moieties is individually selected from the group consisting of hydrogen and alkyl moieties. Ethylene oxide propylene oxide or mixtures of ethylene oxide and propylene oxide are more preferred reactants. Alkylene oxide reactants consisting essentially of ethylene oxide are considered most preferred from the standpoint of commercial opportunities for the practice of alkoxylation processes.

Likewise, the active hydrogen reactants suitably utilized in the process of the invention include those known in the art for reaction with alkylene oxides and conversion to alkoxylate products. Suitable classes of active hydrogen reactants include (but are not necessarily limited to) alcohols, phenols, thiols (mercaptans), amines, polyols, carboxylic acids, and mixtures thereof. Generally, but not necessarily, the active hydrogen moiety is of the form —XH, where X represents an oxygen, sulfur, or (substituted, e.g., amino) nitrogen atom. Preference generally exists for use of hydroxyl-containing reactants. More preferably, the active hydrogen-containing reactant is selected from the group consisting of alkanols, alkyl polyols and phenols (including alkyl-substituted phenols).

Preference can also be expressed for the application of this invention to the alkoxylation of primary active hydrogen containing compounds, that is, compounds wherein the wherein the active hydrogen moiety is attached to a primary carbon atom. As is often the case for alkoxylation reactions, such primary compounds are more reactive in the process of this invention than are the corresponding secondary and tertiary compounds, and the process is generally more selective for the conversi©n of the primary compounds to products having the most desirable alkylene oxide adduct distributions.

Among the suitable carboxylic acids, particular mention may be made of the mono- and dicarboxylic acids, both aliphatic (saturated and unsaturated) and aromatic. Specific examples include acetic acid, propionic acid, butyric acid, valeric acid, caproic acid, lauric acid, myristic acid, palmitic acid, steric acid, oleic acid, rosin acids, tall oil acids, terephthalic acid, benzoic acid, phenylacetic acid, toluic acid, acrylic acid, methacrylic acid, crotonic acid, maleic acid, and the like.

Among the suitable amines, particular mention may be made of primary, secondary and tertiary alkylamines and of alkylamines containing both amino and hydroxyl groups, e.g., N,N-di(n-butyl)-ethanolamine and tripropanolamine.

Among the suitable thiols, particular mention may be made of primary, secondary and tertiary alkane thiols having from 1 to about 30 carbon atoms, particularly those having from about 8 to 20 carbon atoms. Specific examples of suitable tertiary thiols are those having a highly branched carbon chain which are derived via hydrosulfurization of the products of the oligomerization of lower olefins, particularly the dimers, trimers, and tetramers and pentamers of propylene and the butylenes. Secondary thiols are exemplified by the lower alkane thiols, such as 2-propanethiol, 2-butanethiol, and 3-pentanethiols, as well as by the products of the hydrosulfurization of the substantially linear oligomers of ethylene as are produced by the Oxo process. Representative, but by no means limiting, examples of thiols derived from ethylene oligomers include the linear carbon chain products, such as 2-decanethiol, 3-decanethiol, 4-decanethiol, 5-decanethiol, 3-dodecanethiol, 5-dodecanethiol, 2-hexadecanethiol, 5-hexadecanethiol, and 8-octadencanethiol, and the branched carbon chain products, such as 2-methyl-4-tridecanethiol. Primary thiols are typically prepared from terminal olefins by hydrosulfurization under free-radical conditions and include, for example, 1-butanethiol, 1-hexanethiol, 1-dodecanethiol, 1-tetradecanethiol and 2-methyl-1-tridecanethiol.

The alcohols (both mono- and poly-hydroxy) and the phenols (including alkyl-substituted phenols) are preferred classes of active hydrogen reactants for purposes of the invention. Among the phenols, particular mention may be made of phenol and of alkyl-substituted phenols wherein each alkyl substituent has from one to about 30 (preferably from one to about 20) carbon atoms, for example, p-methylphenol, p-ethylphenol, p-hexylphenol, p-decylphenol, didecyl phenol and the like.

Acyclic aliphatic mono-hydric alcohols (alkanols) form a most preferred class of reactants, particularly the primary alkanols, although secondary and tertiary alkanols are also very suitably utilized in the process of the invention. Preference can also be expressed, for reason of both process performance and commercial value of the product, for alkanols having from one to about 30 carbon atoms, with $C_6$ to $C_{24}$ alkanols considered more preferred and $C_8$ to $C_{20}$ alkanols considered most preferred. As a general rule, the alkanols may be of branched or straight chain structure, although preference further exists for alkanol reactants in which greater than about 50 percent, more preferably greater than about 60 percent and most preferably greater than about 70 percent of the molecules are of linear (straight-chain) carbon structure.

The general suitability of such alkanols as reactants in alkoxylation reactions is well recognized in the art. Commercially available mixtures of primary monohydric alkanols prepared via the oligomerization of ethylene and the hydroformylation or oxidation and hydrolysis of the resulting higher olefins are particularly preferred. Examples of commercially available alkanol mixtures include the NEODOL Alcohols, trademark of and sold by Shell Chemical Company, including mixtures of $C_9$, $C_{10}$ and $C_{11}$ alkanols (NEODOL 91 Alcohol), mixtures of $C_{12}$ and $C_{13}$ alkanols (NEODOL 23 Alcohol), mixtures of $C_{12}$, $C_{13}$, $C_{14}$, and $C_{15}$ alkanols (NEODDL 25 Alcohol), and mixtures of $C_{14}$ and $C_{15}$ alkanols (NEODOL 45 Alcohol); the ALFOL Alcohols, trademark of and sold by Vista Chemical Company, including mixtures of $C_{10}$ and $C_{12}$ alkanols (ALFOL 1012), mixtures of $C_{12}$ and $C_{14}$ alkanols (ALFOL 1214), mixtures of $C_{16}$ and $C_{18}$ alkanols (ALFOL 1618), and mixtures of $C_{16}$, $C_{18}$ and $C_{20}$ alkanols (ALFOL 1620); the EPAL Alcohols, trademark of and sold by Ethyl Chemical Company, including mixtures of $C_{10}$ and $C_{12}$ alkanols (EPAL 1012), mixtures of $C_{12}$ and $C_{14}$ alkanols (EPAL 1214), and mixtures of $C_{14}$, $C_{16}$, and C alkanols (EPAL 1418); and the TERGITOL-L Alcohols, trademark of and sold by Union Carbide Corporation, including mixtures of $C_{12}$, $C_{13}$, $C_{14}$, and C alkanols (TERGITOL-L 125). Also very suitable are the commercially available alkanols prepared by the reduction of naturally occurring fatty esters, for example, the CO and TA products of Procter and Gamble Company and the TA alcohols of Ashland Oil Company.

Among the polyols, particular mention may be made of those having from 2 to about 6 hydroxyl groups and 2 or more, preferably 2 to 30 carbon atoms. Specific examples include the alkylene glycols such as ethylene glycol, propylene glycol, hexylene glycol, and decylene glycol, the polyalkylene glycol ethers, such as diethylene glycol, triethylene glycol, propylene glycol, dipropylene glycol, tripropylene glycol, glycerine, sorbitol, and the like. Higher oligomers and polymers of the polyols are also very suitable.

The active hydrogen containing reactant is also very suitably the alkoxylate product of a previous alkoxylation of an active hydrogen containing compound.

Further examples of both specific alkylene oxide reactants and specific active hydrogen containing reactants suitable for use in this invention are recited in the aforementioned U.S. Patents, the relevant disclosures of which are incorporated herein by this reference.

For purposes of the invention, the alkylene oxide reactant and the active hydrogen reactant are necessarily contacted in the presence of a catalyst comprising one or more compounds of one or more of the rare earth elements. The catalyst is applied in a quantity which is effective to catalyze the alkoxylation reaction.

The catalyst in a given application of this process suitably contains compounds of either one or a mixture of the rare earth elements. The rare earth metals are themselves also suitable catalysts for the process of the invention. In one respect, preference can be expressed for catalysts comprising in catalytically effective amount one or more compounds of one or more elements selected from the group comprising cerium, lanthanum, praseodymium, neodymium, yttrium, samarium, gadolinium, dysprosium, erbium and ytterbium. In another respect, catalysts comprising a catalytically effective amount of one or more compounds of one or more of the cerium earth group elements are particularly preferred, while catalysts comprising a catalytically effective amount of one or more compounds of elements selected from the group consisting of cerium and lanthanum are considered most preferred. In a further respect, preferred catalysts comprise a catalytically effective amount of one or more compounds of the lanthanum series elements (atomic numbers 57-71). Still further, a preferred class of catalysts comprise a catalytically effective amount of one or more compounds of the lanthanide series elements (atomic numbers 58-71). In still another respect, preference can be expressed for catalysts comprising in catalytically effective amount one or more compounds of yttrium.

Natural mineral ores which serve as the commercial sources of the rare earth elements generally contain several of the elements. These ores are often refined without separating this mixture into distinct elements. For this reason, the use in the invention of compounds of mixtures of the rare earth elements may be preferred from the standpoint of availability and cost. Specific examples of suitable mixtures of rare earth elements include those known as bastnasite, monazite, xenotime, didymium, gadolinite and euxenite.

In addition to a catalytically effective amount of the rare earth element compounds, the catalyst for the process of the invention may also suitably contain other substances, including both those which may be introduced into the process as impurities in the rare earth element compounds as well as those which may be added to promote or modify catalyst activity.

A class of rare earth compounds preferred for use in the invention includes simple metal (i.e., mono-metallic) salts of the formula Lp - Xq, wherein each L represents a rare earth element, X represents a metal -free anion and p and q are numbers satisfying the valency requirements of the particular rare earth element and the particular anion. (As is well recognized in the art, the simple metal salts principally comprise rare earth elements in the trivalent state. Compounds of the trivalent metals are preferred for use in the invention. However, the invention is also intended to encompass divalent metal salts and tetravalent metal salts.) Such simple metal salts, as this terminology is used herein, are intended to specify mono-metallic compounds, to the extent that the one or more rare earth element atoms present represent the only metallic element(s) in the catalyst compound(s). Specific examples of suitable inorganic catalysts in this class include the halides such as lanthanum chloride ($LaCl_3$), the oxides such as cerium oxide ($Ce_2O_3$), the hydroxides such as yttrium hydroxide ($Y(OH)_3$), the sulfides such as lanthanum sulfide ($La_2S_3$), the carbides such as lanthanum carbide, the carbonates such as samarium carbonate ($Sm_2(CO_3)_3$), the borides such as lanthanum boride the hydrides such as yttrium hydride ($Y(H)_3$), the nitrates such as neodymium nitrate ($Nd(NO_3)_3$) the nitrides such as lanthanum nitride (LaN), the amides such as cerium amide ($Ce(NH_2)_3$) and the perchlorates such as cerium perchlorate ($Ce(ClO_4)_3$). Specific examples of organic catalysts in this class include the carboxylates such as cerium acetate ($Ce(OOCCH_3)_3$), the oxalates such as praseodymium oxalate ($Pr_2(C_2O_4)_3$), the alkoxides and phenoxides ($L(OR)_3$) for which each R is an alkyl or optionally alkyl-substituted phenol group and L represents a rare earth element, thiolates such as samarium thiolate ($Sm(SR)_3$), thiophenoxides such as neodymium thiophenoxide ($Nd(SC_6H_5)_3$) and beta-diketones such as lanthanum 2,4-pentanedionate. Compounds of trivalent rare earth metals are particularly preferred. Simple metal salts do not include cationic lanthanum ionexchanged on aluminosilicates or clays, as disclosed or suggested by the aforementioned European patent application 0250168.

A preferred group of catalyst compounds are the alkoxides (or alcoholates) and the phenoxides (or phenolates), particularly where the active hydrogen containing reactant consists essentially of an alcohol (or, in preferred embodiments, an alkanol) or phenol or an alkyl-substituted phenol. It will be understood that such compounds can take several forms. Thus, for instance, in the case of a catalyst compound which is an alcoholate or phenolate of the element cerium (Ce III), the preferred catalyst compounds have the formula

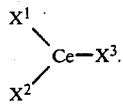

(Catalyst compounds of other rare earth elements can be similarly represented with the number of X substituents reflecting in each case the element's valence state.) At least one of the X substituents in such a formula then represents an alcoholate or phenolate —OR moiety. For the preferred alkoxide and phenoxide compounds, the R group in the —OR moiety is selected from the group consisting of alkyl and (optionally alkyl substituted) phenyl moieties, more preferably $C_1$ to $C_{30}$ alkyl and optionally alkyl-substituted phenyl moieties. The X substituent(s) which represent —OR groups suitably represent the same or different —OR groups. Since the invention contemplates the possibility of the use of precursor compounds, any or all ⓒf the X groups can also represents a precursor moiety which undergoes conversion to an —OR moiety in the process mixture, and particularly in the presence of the active hydrogen containing reactant. The one or more of the X substituents which are not either —OR groups or precursors for the formation of —OR groups suitably represent other organic or inorganic moieties which do not adversely interfere with the desired catalytic activity for the alkoxylation. Very suitably, all of the X groups represent (or are in practice converted to) the same or different —OR groups.

Specific examples of preferred alkoxide compounds generally suitable as catalyst components for purposes of the invention include the lanthanum, cerium, neodymium, yttrium, and praseodymium alkoxides (wherein R is $C_1$ to $C_{30}$ alkyl), including the lower alkoxides, e.g., praseodymium pentoxide, cerium isopropoxide, and yttrium t-butoxide, as well as the higher alkoxides having one or more of their alkyl R substituents in the same $C_8$ to $C_{20}$ range as the most preferred alkanol reactant of the process, e.g., nonyl, decyl, dodecyl, hexadecyl, etc. Specific examples of preferred phenoxide compounds useful in this service include lanthanum phenoxide, lower alkyl-substituted phenol derivatives such as cerium benzyloxide and and higher alkyl-substituted phenol derivatives, e.g., compounds wherein R represents nonylphenyl, tridecylphenyl, pentadecylphenyl, etc.

When the process is applied to alkoxylation of an alkanol reactant, particular preference exists for the use of alkoxide catalyst compound(s) in which the one or more "X" substituents which represent —OR groups (and most preferably all of the X substituents) are characterized by an alkyl group R which has a carbon number in the range from 1 to about 30, more preferably a carbon number in the range from about 1 to 20, and most preferably a carbon number which corresponds closely to the carbon number(s) of the particular alkanol reactant employed in a given process application. Thus, for instance, the reaction of a dodecyl alcohol reactant is most preferably conducted in the presence of a catalytic alkoxide compound for which the —OR substituents present have dodecyl alkyl groups R.

Without intention that the invention be limited to one theory or mechanism of operation, it is thought that at least certain of the simple metal salt compounds of the rare earth elements, as well as possibly the metals themselves and other of their compounds, may undergo reaction with the active hydrogen containing reactant (and possibly also the alkoxylate product) to produce corresponding derivatives of the reactant (and of the alkoxylate product) which are the predominant active catalyst species in the typical alkoxylation reaction. Thus, for example, when the compound cerium n-butoxide is contacted with a higher alkanol alkoxylation reactant (e.g., a $C_{12}$ alkanol), a transalcoholysis reaction occurs which liberates butanol and converts at least a portion of the cerium butoxide to cerium alkoxides havin $C_{12}$ alkyl substituents. In this respect, the invention specifically encompasses rare earth element compounds of the formula shown above wherein the X substituents which are —OR (or —SR, —NR, etc.) groups correspond to the reactant (absent the active hydrogen atom). Equivalently, the X substituents in such a formula may suitably correspond to alkoxylate molecules as are produced in the alkoxylation process (again absent an active hydrogen atom), for example, corresponding ethoxylates of the formulas $(OCH_2CH_2)_nOR$; $(OCH_2CH_2)_nSR$; and $(OCH_2)_nNR$.

The one or more compounds of the rare earth elements are present in the reaction mixture in a catalytically effective amount. Although a specific quantity of catalyst is not critical to the invention, preference may be expressed for use of the catalyst in amount of at least about 0.01 percent by weight (% w), while an amount between about 0.02 and 5% w is considered more preferred and an amount between about 0.5 and 2% w is considered most preferred for typical embodiments. These percentages are in terms of the weight of rare earth metals or metal ions in the process mixture relative to the weight of active hydrogen containing compounds in that mixture. Substantially greater quantities of catalyst, e.g., up to about 10% w or more, are also very suitable. As a rule, the higher the desired average alkylene oxide adduct number of the alkoxylate product and the higher the desired rate of reaction, the greater the required quantity of catalyst.

With respect to the use of rare earth element compounds as alkoxylation catalysts in combination with other materials which modify or promote the activity of such catalysts, it has further been found that the adduct distribution of the alkoxylate product is narrowed and-/or the activity of the catalyst is enhanced by applying the compounds in combination with acids. Preferably, the invention is carried out in the presence of a combination of a rare earth element compound with an oxo acid of sulfur or an oxo acid of phosphorus. Examples of oxo acids of sulfur include sulfur trioxide ($SO_3$) and acids of the class represented by the empirical formula $ZSO_3H$. Included within this class are, for instance, sulfuric acid (with Z in the formula representing —OH), monoalkyl esters of sulfuric acid which are also commonly called alkyl sulfuric acids (with Z representing an alkoxy group), sulfurous acid (wherein Z represents H), and sulfonic acids wherein Z represents a univalent inorganic atom or organic radical. Preferred alkyl sulfuric acids include those with an alkyl group of about 1 to 30 carbon atoms. Alkyl sulfuric acids having an alkyl group of about 1 to 20 carbon atoms are more preferred, while those having an alkyl group of about 8 to 20 carbon atoms are considered most preferred. Specific examples of suitable inorganic sulfonic acids include chlorosulfonic acid (wherein Z is Cl), fluorosulfonic acid (wherein Z is F) and sulfamic acid (wherein Z is $NH_2$). Examples of organic sulfonic acids include the alkane- and cycloalkane sulfonic acids, as well as arenesulfonic acids and heterocyclic sulfonic acids. Specific examples of the alkane sulfonic acids include methanesulfonic acid, ethanesulfonic acid, propanesulfonic acid, butanesulfonic acid, pentanesulfonic acid, hexanesulfonic acid, dodecanesulfonic acid, hexadecanesulfonic acid, trifluoromethane sulfonic acid, sulfosuccinic acid, and cyclohexylsulfonic acid. Specific examples of arenesulfonic acids include benzenesulfonic acid, toluenesulfonic acid, styrene (i.e., vinyl benzene) sulfonic acid, 5-sulfosalicylic acid, phenolsulfonic acid, and 1,6-naphthalene disulfonic acid. Specific examples of heterocyclic sulfonic acids include sulfanilic acid. Alkyl and aryl groups of the sulfonic acid molecule are suitably substituted with relatively inert organic and/or inorganic substituents. Examples of substituted organic sulfonic acids include 4-hydroxybenzoic acid, trifluoromethane sulfonic acid, isethionic acid, and taurine. A particularly preferred group of oxo sulfur acids is that which consists of sulfuric acid, sulfur trioxide, $C_1$ to $C_{30}$ alkyl sulfuric acids, sulfanilic acid, toluenesulfonic acid, styrenesulfonic acid, methanesulfonic acid, and 5-sulfosalicylic acid. An acid selected from the group consisting of sulfuric acid, sulfur trioxide, and the $C_1$ to $C_{30}$ alkyl sulfuric acids is considered more preferred, and sulfuric acid is considered a most preferred oxo sulfur acid for use in the invention.

Oxo acids of phosphorus include phosphoric and phosphorus acids. The hypo-, meta-, ortho-, and pyro- forms of both phosphoric and phosphorus acids are useful, as are related derivatives such as monofluoro- and difluorophosphoric acids. Other examples are the oxides of phosphorus, including the trioxide, tetraoxide, and pentaoxide. The acids may be partially neutralized and contain, for instance, alkali metal or alkaline earth metal cations. Examples of partially neutralized oxo metal acids of phosphorus include the alkali metal and alkaline earth metal dihydrogen phosphates and dihydrogen diphosphates. Specific examples are sodium dihydrogen phosphate, disodium hydrogen phosphate, potassium dihydrogen phosphate, and calcium hydrogen phosphate. Also suitable are the alkyl, aryl, alkylaryl, and arylalkyl dihydrogen phosphates, otherwise known as the esters of phosphoric acid, such as methyl dihydrogen phosphate, benzene dihydrogen phosphate, and ethyl dihydrogen phosphate. Oxo acids of phosphorus are also exemplified by the alkyl, aryl, alkylaryl and arylalkyl phosphinic and phosphonic acids. Specific examples include benzene phosphinic acid, benzene phosphonic acid, ethyl phosphinic acid, ethyl phosphonic acid, methyl phosphinic acid, and methyl phosphonic acid. Still other examples of the oxo acids of phosphorus are phosphomolybdic acid and phosphotungstic acid. A particularly useful class of orthophosphoric acid and ortho phosphoric acid derivatives may be represented by the formula

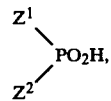

wherein $Z^1$ and $Z^2$ each individually represents a univalent inorganic atom or organic radical. Preferably, each of $Z^1$ and $Z^2$ are independently selected from the group consisting of OH, OM, R and OR groups, with H representing hydrogen, M an alkali metal and R an alkyl, aryl, arylalkyl, or alkylaryl group. For example, $Z^1$ and $Z^2$ suitably each represent OH (in which case the formula identifies phosphoric acid), $Z^1$ may represents an OM group with M representing an alkali metal and $Z^2$ may represent OH (in which case the formula identifies an alkali metal dihydrogen phosphate), $Z^1$ may represent R (with R representing an alkyl, aryl, arylalKyl or alkylaryl group) and $Z^2$ may represent OH (in which case the formula represents the corresponding phosphonic acid), $Z^1$ and $Z^2$ may each represent an R group (in which case the formula identifies the corresponding phosphinic acid), $Z^1$ may represent OR and $Z^2$ may represent OH (in which case the formula identifies the corresponding alkyl, aryl, arylalkyl or alkylaryl dihydrogen phosphate). Similarly, a suitable class of hypophosphoric acid and its derivatives may be represented by the formula

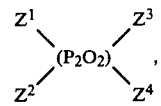

and a class of pyro-phosphoric acid and its derivatives may be represented by the formula

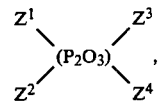

wherein $Z^1$, $Z^2$, $Z^3$, and $Z^4$ each individually represents a univalent inorganic atom or organic radical. Preferably, each of $Z^1$, $Z^3$, and $Z^4$ is independently selected from the group consisting of OH, OM, R and OR groups, as hereinabove defined. A particularly preferred group of oxo acids of phosphorus is that which consists of the ortho-, hypo-, and pyroforms of both phosphoric and phosphorous acid, the metal and alkyl, aryl, arylalkyl, and alkylaryl dihydrogen phosphates, and the alkyl, aryl, arylalkyl, and alkylaryl phosphinic and phosphonic acids. An acid selected from the group consisting of ortho-, hypo-, and pyro- phosphoric acids, ortho-, hypo-, and pyro- phosphorous acids, and alkyl, aryl, alkylaryl, and arylalkyl dihydrogen phosphates is considered more preferred. The phosphoric acids, particularly orthophosphoric acid, and the phosphorous acids, particularly orthophosphorous acid, are considered most preferred among the oxo acids of phosphorus.

When an organic oxo acid of sulfur or phosphorus is employed in the process of the invention, it is preferred that the compound contain between 1 and about 30 carbon atoms. Organic acids containing from 1 to about 20 carbon atoms are more preferred, and those containing between about 1 and 7 carbon atoms are considered most preferred.

The optional acid can be added directly to the process mixture or formed therein upon addition to the mixture of precursor compounds. For example, in the presence of the alkanol reactant, the phosphorus oxides act as precursors for the formation of mono-esters of phosphoric acid and are thus considered phosphorus-containing acids for purposes of this invention.

The advantages associated with production of a narrow-range adduct distribution alkoxylate product can also be realized simply by utilizing compounds of the rare earth elements which contain one or more anions which correspond to those of the aforementioned oxo acids of sulfur or phosphorus. Thus, for example, the simple cerium sulfate and cerium phosphate salts are found to be highly active and to catalyze the production of alkoxylates of exceptionally narrow-range adduct distribution. In a particularly important embodiment, the invention is a process which comprises contacting and reacting one or more alkylene oxides (particular ethylene oxide, propylene oxide, or a mixture of propylene oxide and ethylene oxide) with one or more active hydrogen containing compounds (particularly alcohols, polyols, or other hydroxyl containing compounds), in the presence of a catalyst which comprises one or more compounds of the formula $L_p\text{-}X_q$, wherein L is a rare earth element, X is an oxo sulfur or oxo phosphorus anion and p and q satisfy the relevant valency relationship. Thus, for instance, a sulfate salt of a trivalent compound has the formula $L_2(SO_4)_3$, and a phosphate salt of a trivalent compound has the formula $L_2(PO_4)$. Particularly preferred phosphate salt catalysts and alkoxylation processes utilizing those catalysts are described and claimed in the commonly-assigned copending application Ser. No. 482379, having attorney's docket number T-2151G. The disclosure of that copending application is incorporated herein by this reference. In a most preferred embodiment, ethylene oxide is contacted with a $C_1$ to $C_{30}$ primary alkanol in the presence of such a catalyst, particularly a catalyst which comprises phosphate and/or sulfate salt(s) of one or more of the rare earth elements.

In terms of processing procedures, the alkoxylation reaction in the invention may be conducted in a generally conventional manner. For example, the catalyst may initially be mixed with liquid active hydrogen reactant. The catalyst is suitably either soluble (either partially or completely) or insoluble in this liquid reactant as well as in liquid mixtures of the reactant and the product formed as the process is carried out. In particularly preferred embodiments, e.g., alkoxylations of alkanols catalyzed by the phosphate and/or sulfate salt(s), the catalyst is essentially insoluble in the reactants and the reaction product. The mixture of catalyst and liquid reactant is contacted, preferably under agitation, with alkylene oxide reactant, which is typically introduced in gaseous form at least for the lower alkylene oxides. The order in which the reactants and catalyst are contacted has not been found to be critical to the invention.

While these procedures describe a batch mode of operation, the invention is equally applicable to a continuous process.

Overall, the two reactants are utilized in quantities which are predetermined to yield an alkoxylate product of the desired mean or average adduct number. The average adduct number of the product is not critical to this process. Such products commonly have an average adduct number in the range from less than one to about 30 or greater.

In general terms, suitable and preferred process temperatures and pressures for purposes of this invention are the same as in conventional alkoxylation reactions between the same reactants, employing conventional catalysts. A temperature of at least about 90° C., particularly at least about 120° C. and most particularly at least about 130° C., is typically preferred from the standpoint of the rate of reaction, while a temperature less than about 250° C., particularly less than about 210° C., and most particularly less than about 190° C., is typically desirable to minimize degradation of the product. As is known in the art, the process temperature can be optimized for given reactants, taking such factors into account.

Superatmospheric pressures, e.g., pressures between about 10 and 150 psig, are preferred, with pressure being sufficient to maintain the active hydrogen reactant substantially in the liquid state.

When the active hydrogen reactant is a liquid and the alkylene oxide reactant is a vapor, alkoxylation is then suitably conducted by introducing alkylene oxide into a pressure reactor containing the liquid active hydrogen reactant and the catalyst. For considerations of process safety, the partial pressure of a lower alkylene oxide reactant is preferably limited, for instance, to less than about 60 psia, and/or the reactant is preferably diluted with an inert gas such as nitrogen, for instance, to a vapor phase concentration of about 50 percent or less. The reaction can, however, be safely accomplished at greater alkylene oxide concentration, greater total pressure and greater partial pressure of alkylene oxide if suitable precautions, known to the art, are taken to manage the risks of explosion. A total pressure of between about 40 and 110 psig, with an alkylene oxide partial pressure between about 15 and 60 psig, is particularly preferred, while a total pressure of between about 50 and 90 psig, with an alkylene oxide partial pressure between about 20 and 50 psig, is considered more preferred.

The time required to complete a process according to the invention is dependent both upon the degree of alkoxylation that is desired (i.e., upon the average alkylene oxide adduct number of the product) as well as upon the rate of the alkoxylation reaction (which is, in turn dependent upon temperature, catalyst quantity and nature of the reactants). A typical reaction time for preferred embodiments is in the range from 1 to 24 hours. In some instances the process is characterized by an induction period after the reactants and catalyst are contacted and before the alkoxylation reaction commences at a meaningful rate.

After the ethoxylation reaction has been completed, the product is preferably cooled. If desired, catalyst can be removed from the final product, although catalyst removal is not necessary to the process of the invention. Catalyst residues may be removed, for example, by precipitation or extraction or the like.

The following Examples are provided to further illustrate certain specific aspects of the invention but are not intended to limit its broader scope.

EXAMPLE 1

An alkoxylation process in accordance with the invention was conducted under the following procedures. The alkylene oxide reactant for this process embodiment consisted of ethylene oxide and the active hydrogen containing reactant consisted of NEODOL 23 Alcohol (NEODOL is a trademark of Shell Chemical Company) characterized as a mixture of primary, 80% linear (20% branched) alkanols having twelve and thirteen carbon atoms (about 40% by mole $C_{12}$ and 60% by mole $C_{13}$). The catalyst was lanthanum n-butoxide, prepared by reacting n-butanol with lanthanum methoxide which, in turn, had been prepared by reacting lithium methoxide with lanthanum chloride methanolate.

Initially, 1.54 grams (0.0043 mols) of the lanthanum n-butoxide was added to 200 grams (1.03 mols) of the alcohol reactant. The resulting slurry was nitrogen sparged for one hour at 130° C. and then transferred to a one liter autoclave reactor maintained under nitrogen atmosphere. Temperature of the reactor and its contents was raised to 170° C. A mixture of nitrogen and ethylene oxide was then introduced into the reactor to a total pressure of 75 psia (45 psia nitrogen and 30 psia ethylene oxide). Alkoxylation (ethoxylation) commenced immediately. Additional ethylene oxide was supplied on demand to maintain an essentially constant 75 psia pressure. Temperature was maintained at 170° C. The process was characterized by a slow, steady uptake of ethylene oxide. After a total reaction time of 6 hours, ethylene oxide addition was discontinued. The reactor was maintained at 170° C. for an additional one hour to consume unreacted ethylene oxide in the system. The product mixture was then cooled and neutralized with acetic acid.

The product was analyzed by GC-LC techniques and found to have a mean average adduct number of 0.72. The ethylene oxide adduct distribution of the product is presented in the following table. The only observed by-products were polyethylene glycols (PEG) in a quantity of about 1 percent by weight.

| Ethoxylate Distribution | |
|---|---|
| Adduct Number | Concentration |
| 0 (Residual Alcohol) | 49.96% w |
| 1 | 23.64 |
| 2 | 15.21 |
| 3 | 6.94 |
| 4 | 2.73 |
| 5 | 1.02 |
| 6 | 0.50 |

EXAMPLE 2

In another alkoxylation process embodiment according to the invention, 1.0 grams (0.003 mols) of tricyclopentadienyl lanthanum was added to 72 grams (0.371 mols) of the same NEODOL 23 Alcohol reactant. The resulting mixture was nitrogen sparged for one hour at 130° C. and then transferred under nitrogen atmosphere to the one liter autoclave reactor. Alkoxylation was carried out as described in Example 1. The reaction proceeded at a significant rate after an induction period of about 15 minutes. After a total reaction time of 3 hours, ethylene oxide addition was discontinued. The reactor was maintained at 170° C. for an additional one hour to consume unreacted ethylene oxide in the system. The product mixture cooled and neutralized with acetic acid.

The product was analyzed and found to have a mean average adduct number of 2.9. The ethylene oxide adduct distribution of the product is presented in the following table. The only observed by-product was PEG in a quantity of about 1 percent by weight.

| Ethoxylate Distribution | |
|---|---|
| Adduct Number | Concentration |
| 0 (Residual Alcohol) | 11.9% w |
| 1 | 7.8 |
| 2 | 11.9 |
| 3 | 16.6 |
| 4 | 17.7 |
| 5 | 14.3 |
| 6 | 9.7 |
| 7 | 5.4 |
| 8 | 2.6 |
| 9 | 1.1 |
| 10 | 0.5 |
| 11 | 0.2 |
| 12 | 0.1 |
| 13 | 0.1 |

EXAMPLE 3

The general procedures of Example 1 were repeated using as catalyst a combination of lanthanum isopropoxide and sulfuric acid. Initially, a solution of 2.0 grams (0.0063 mols) of lanthanum isopropoxide dissolved in 125 grams of 2-ethoxyethanol was added to 200 grams of the NEODOL 23 Alcohol. This solution was stirred and heated to 70° C. Then, 0.52 grams (0.005 mols) of 96% w sulfuric acid was added over a period of ten minutes. 2-Ethoxyethanol and isopropanol (resulting from a transalcoholysis reaction of the lanthanum isopropoxide with the NEODOL 23 Alcohol) were removed by distillation under vacuum. The remaining mixture was transferred to a one-liter autoclave reactor maintained under nitrogen atmosphere. The temperature of the reactor was raised to 140° C. and an ethylene oxide/nitrogen mixture was introduced as described in Example 1. After 5 hours, a total of 308 grams of ethylene oxide had been added to the reaction. The reactor was maintained at 140° C. for an additional 30 minutes to consume unreacted ethylene oxide.

The product was analyzed by GC-LC and found to have a mean average adduct number of 7.1. The narrow-range ethylene oxide adduct distribution of the product is illustrated in the following table. The only observed by-product was PEG in a quantity of about 1.3% w.

| ETHOXYLATE DISTRIBUTION | |
|---|---|
| Adduct Number | Concentration |
| 0 (Residual Alcohol) | 1.8% w |
| 1 | 0.6 |
| 2 | 0.7 |
| 3 | 1.2 |
| 4 | 2.8 |
| 5 | 6.4 |
| 6 | 13.0 |
| 7 | 18.7 |
| 8 | 19.4 |
| 9 | 15.2 |
| 10 | 9.4 |
| 11 | 5.1 |
| 12 | 2.6 |
| 13 | 1.3 |
| 14 | 0.7 |
| 15 | 0.5 |
| 16 | 0.3 |
| 17 | 0.2 |
| 18 | 0.2 |
| 19 | 0.2 |

EXAMPLE 4

The procedures of Example 3 were repeated. A total of 258 grams of ethylene oxide was taken up by the reaction, resulting in a product having an average adduct number of 5.5.

EXAMPLE 5 (18393-134)

The general procedures of Example 3 were again followed. In this case, a solution of 2.0 grams (0.0063 mols) of lanthanum isopropoxide in 50 grams of 2-ethoxyethanol was mixed with 200 grams of the alcohol. This mixture was heated to 70° C. and 0.68 grams (0.0064 mols) of 96% w sulfuric acid was added dropwise over a period of ten minutes. After stirring at 70° C. for an additional 30 minutes, 2-ethoxyethanol and isopropanol were removed by vacuum distillation.

Ethoxylation was carried out as described in Example 3, with 310 grams of ethylene oxide taken up over a 4.5 hour period. The product had a mean average adduct number of 7.0 and a narrow range distribution, and contained 2.2% w residual alcohol and 0.9% w PEG.

EXAMPLE 6

The procedures of Example 5 were repeated. A total of 312 grams of ethylene oxide was taken up by the reaction, resulting in a product having an average adduct number of 7.0.

EXAMPLE 7

Following the general procedures of Example 3, a solution of 2.0 grams (0.0063 mols) of lanthanum isopropoxide in 50 grams of 2-ethoxyethanol was mixed with 200 grams of the alcohol. This mixture was heated to 70° C. and 0.29 grams (0.0028 mols) of 96% w sulfuric acid was added dropwise over a period of ten minutes. After stirring at 70° C. for an additional 30 minutes, 2-ethoxyethanol and isopropanol were removed by vacuum distillation.

Ethoxylation was carried out over the temperature range of 140°–170° C. A total of 107 grams of ethylene oxide was taken up over a 4.5 hour period. The product had a mean average adduct number of 2.3 and contained 2.5% w PEG.

EXAMPLE 8

Following the general procedures of Example 3, a solution of 2.0 grams (0.0063 mols) of lanthanum isopropoxide in 50 grams of 2-ethoxyethanol was mixed with 200 grams of the alcohol. This mixture was heated to 70° C. and 0.97 grams (0.0094 mols) of 96% w sulfuric acid was added dropwise over a period of ten minutes. After stirring at 70° C. for an additional 30 minutes, 2-ethoxyethanol and isopropanol were removed by vacuum distillation.

Ethoxylation was carried out over the temperature range of 140°–170° C. A total of 73 grams of ethylene oxide was taken up over a 6 hour period. The product had a mean average adduct number of 0.93 and contained 7.3% w PEG.

EXAMPLE 9

The general procedures of Example 8 were repeated, with a solution of 2 grams of lanthanum isopropoxide in 100 grams of ethylene glycol dimethyl ether. This solution was added to 200 grams of the alcohol and the resulting mixture was treated with 0.661 grams (0.0064 mols) of 96% sulfuric acid. A total of 303 grams of ethylene oxide was taken up over a reaction time of 4 hours, producing an ethoxylate with a mean average adduct number of 7.0, containing 1.4% w PEG and having the following narrowrange adduct distribution:

| ETHOXYLATE DISTRIBUTION | |
|---|---|
| Adduct Number | Concentration |
| 0 (Residual Alcohol) | 3.1% w |
| 1 | 1.2 |

| ETHOXYLATE DISTRIBUTION | |
|---|---|
| Adduct Number | Concentration |
| 2 | 1.3 |
| 3 | 2.0 |
| 4 | 3.3 |
| 5 | 5.3 |
| 6 | 9.1 |
| 7 | 13.0 |
| 8 | 15.5 |
| 9 | 15.3 |
| 10 | 12.5 |
| 11 | 8.6 |
| 12 | 5.0 |
| 13 | 2.5 |
| 14 | 1.3 |
| 15 | 0.5 |
| 16 | 0.3 |
| 17 | 0.1 |
| 18 | 0.1 |

EXAMPLE 10

Two grams (0.0063 mols) of lanthanum isopropoxide were dissolved in 125 grams of 2-ethoxyethanol and 200 grams of NEODOL Alcohol. 2-Ethoxyethanol and isopropanol were removed by vacuum distillation. The resulting solution was transferred to a one-liter autoclave reactor and contacted with ethylene oxide according to the reaction procedures of Example 3. A total of 305 grams of ethylene oxide was taken up over an 8 hour period producing an ethoxylate with a mean average adduct number of 7.1.

EXAMPLE 11

Eight grams of lanthanum oxide were suspended in 465 grams of 2-ethoxyethanol and heated to reflux for 19 hours. The mixture was cooled to 70° C., at which time 800 grams of NEODOL 23 Alcohol was added. A total of 0.9 grams of 96% w $H_2SO_4$ was slowly added and the mixture was stirred for an additional 30 minutes. Approximately 407 grams of 2-ethoxyethanol were removed via vacuum distillation. A total of 785 grams of the remaining mixture and an additional 41 grams of the alcohol was added to the autoclave and contacted with ethylene oxide at a temperature which varied from 40° C. to 170° C., according to the general reaction procedures of Example 3. A total of 61 grams of ethylene oxide was taken up over a 3 hour period. Both the alcohol and the 2-ethoxyethanol were ethoxylated.

EXAMPLE 12

An ethoxylation catalyst was prepared by the following procedure. A first solution was prepared by dissolving 10.4 grams of $LaC_{13}.6H_2$ mixture of 200 grams of 2-ethoxyethanol and 301 grams of NEODOL 23 Alcohol. This solution was heated to 155° C. and 83 grams of 2-ethoxyethanol were removed along with essentially all of the water. The solution was cooled and determined to have a water content of 79 ppm.

A second solution was prepared by dissolving 5.83 grams of 85% w potassium hydroxide in 500 grams of the alcohol. This solution was heated to 130° C. under nitrogen sparge for several hours until its water content was 175 ppm. A total of 106 grams of 2-ethoxyethanol was added to this solution, and the mixture was heated to 80° C.

The first solution was added dropwise to the second solution over a 2 hour period while maintaining a temperature of 80° C. The solution became cloudy immediately and remained a slurry. Heating was continued with stirring for an additional 14 hours. Stirring was then discontinued and the mixture filtered to remove precipitated potassium chloride.

To 242 grams of the resulting solution, analyzed to contain 0.0072 mols of lanthanum, was added dropwise over 10 minutes at 70° C. 0.816 grams of 85% w phosphoric acid. The mixture was heated an additional 30 minutes at 70° C. After heating to evaporate off essentially all 2-ethoxyethanol, the remaining solution (178 grams) was transferred to an autoclave reactor and ethoxylated at a temperature of 140° C., according to the general procedures of Example 3, for a reaction period of 90 minutes. A total of grams of ethylene oxide were consumed, producing an alkanol ethoxylate having a mean average adduct number of 7.0. The adduct distribution is illustrated in the following table.

| ETHOXYLATE DISTRIBUTION | |
|---|---|
| Adduct Number | Concentration |
| 0 (Residual Alcohol) | 1.6% w |
| 1 | 0.5 |
| 2 | 0.4 |
| 3 | 0.9 |
| 4 | 2.6 |
| 5 | 7.4 |
| 6 | 15.8 |
| 7 | 22.5 |
| 8 | 20.7 |
| 9 | 13.6 |
| 10 | 6.6 |
| 11 | 3.1 |
| 12 | 1.6 |
| 13 | 0.9 |
| 14 | 0.6 |
| 15 | 0.5 |
| 16 | 0.3 |
| 17 | 0.3 |
| 18 | 0.2 |

EXAMPLE 13

The general procedures of Example 12 were repeated, substituting n-butanol for 2-ethoxyethanol. The two solutions were prepared and mixed and the precipitate filtered to produce 118 grams of a solution containing 0.0036 mols of lanthanum. A total of 0.41 grams (0.0035 mols) of 85% w H3PO4 was added dropwise, as the mixture was stirred for 30 minutes. After heating to evaporate off essentially all butanol, the remaining solution (101 grams) wa diluted with an additional 85 grams of dry NEODOL 23 Alcohol. This solution was then transferred to an autoclave reactor and ethoxylated at a temperature of 140° C. to 155° C., according t ©the general procedures of Example 3, for a reaction period of 4 hours. A total of 281 grams of ethylene oxide were consumed, producing an alkanol ethoxylate having a mean average adduct number of 7.0. The adduct distribution is illustrated in the following table.

| ETHOXYLATE DISTRIBUTION | |
|---|---|
| Adduct Number | Concentration |
| 0 (Residual Alcohol) | 2.2% w |
| 1 | 0.8 |
| 2 | 0.9 |
| 3 | 1.5 |
| 4 | 3.1 |
| 5 | 6.7 |
| 6 | 12.2 |
| 7 | 17.5 |
| 8 | 18.9 |

| ETHOXYLATE DISTRIBUTION | |
|---|---|
| Adduct Number | Concentration |
| 9 | 15.6 |
| 10 | 10.2 |
| 11 | 5.9 |
| 12 | 2.6 |
| 13 | 1.2 |
| 14 | 0.5 |
| 15 | 0.3 |
| 16 | 0.2 |
| 17 | 0.1 |
| 18 | 0.0 |

EXAMPLE 14

A lanthanum phosphate compound was prepared by the following procedures. A first solution was prepared by dissolving 10 grams of $LaCl_3.6H_2O$ in 200 grams of deionized water. A second solution was prepared by dissolving 10.64 grams of sodium orthophosphate ($Na_3$-POhd 4.12H$_2$O) in 200 grams of water. The first solution (at room temperature) was added dropwise over a period of 25 minutes to the second solution (at 50° C.}, The resulting mixture was stirred for an additional 30 minutes at 50° C., and then filtered hot to separate a white precipitate. The filter cake was washed three times with 100 ml of 50° C. deionized water. After drying, 7.4 grams of filtrate was recovered as powder.

Three grams of the powder was added to 200 grams of NEODOL 23 Alcohol, and the mixture was heated to 130° C. under nitrogen sparge for 3 hours to drive off water. The resulting slurry was transferred to an autoclave reactor and ethoxylated at 140° C., under the general procedures of Example 3. A total of 315 grams of ethylene oxide was taken up over a period of 2.5 hours, yielding a product having a mean average adduct number of 6.6. The narrow range adduct distribution of this product is presented in the following table.

| ETHOXYLATE DISTRIBUTION | |
|---|---|
| Adduct Number | Concentration |
| 0 (Residual Alcohol) | 1.9% w |
| 1 | 0.8 |
| 2 | 0.8 |
| 3 | 1.3 |
| 4 | 3.6 |
| 5 | 10.0 |
| 6 | 18.4 |
| 7 | 22.3 |
| 8 | 17.6 |
| 9 | 10.4 |
| 10 | 5.4 |
| 11 | 2.9 |
| 12 | 1.5 |
| 13 | 1.0 |
| 14 | 0.7 |
| 15 | 0.5 |
| 16 | 0.4 |
| 17 | 0.4 |
| 18 | 0.3 |

EXAMPLE 15

A lanthanum sulfate compound was prepared by the following procedures. A solution was prepared by dissolving 4.7 grams of 96% w sulfuric acid in 50 grams of deionized water. To this solution was added with stirring, at 50° C., 5 grams of $La_2O_3$ (commercial grade). Water was evaporated at 100° C., leaving a solid which was dried overnight under vacuum at 110° C. 9.3 Grams of solid was recovered.

Three grams of the solid was added to 200 grams of NEODOL 23 Alcohol, and the mixture was heated to 130° C. under nitrogen sparge for 2 hours to drive off water. The resulting mixture was transferred to an autoclave reactor and ethoxylated at 170° C. and at a pressure of 80 psia (30 psia nitrogen and 50 psia elhylene oxide). A total of 316 grams of ethylene oxide was taken up over a period of 4 hours, yielding a product having a mean average adduct number of 6.8. The adduct distribution of this product is presented in the following table.

| ETHOXYLATE DISTRIBUTION | |
|---|---|
| Adduct Number | Concentration |
| 0 (Residual Alcohol) | 2.5% w |
| 1 | 1.1 |
| 2 | 1.2 |
| 3 | 1.8 |
| 4 | 3.9 |
| 5 | 8.4 |
| 6 | 13.7 |
| 7 | 17.3 |
| 8 | 16.2 |
| 9 | 12.1 |
| 10 | 7.8 |
| 11 | 4.7 |
| 12 | 2.9 |
| 13 | 1.7 |
| 14 | 1.2 |
| 15 | 0.9 |
| 16 | 0.7 |
| 17 | 0.5 |
| 18 | 0.4 |

EXAMPLE 16

A catalyst was prepared according to the following procedure. A total of 0.687 grams of a 1:1 mixture by mol of monobutyl phosphate and dibutyl phosphate was added to 110 grams of a mixture containing 0.0036 mols of lanthanum in 2-ethoxyethanol and NEODOL 23 Alcohol at 70° C. with stirring. The 2-ethoxyethanol was removed via vacuum distillation leaving 92.5 grams of a catalyst mixture. This was diluted with additional alcohol producing a total weight of 185 grams. The mixture was transferred to the autoclave reactor and ethoxylated at a temperature of 170° C., according to the general procedures of Example 3, for a reaction period of 4 hours. A total of 103 grams of ethylene oxide were consumed, producing an alkanol ethoxylate having a mean average adduct number of 2.5.

EXAMPLE 17

A catalyst was prepared according to the procedures of Example 16 except that 1.58 grams of 1:1 mixture by mol of monolauryl phosphate and dilauryl phosphate was used with the mixture containing 0.0036 mols of lanthanum in 2-ethoxyethanol and NEODOL 23 Alcohol. After removal of the 2-ethoxyethanol and dilution with additional alcohol, the mixture (172 grams) was transferred to the autoclave reactor and ethoxylated at 170° C. for 4 hours. A total of 107 grams of ethylene oxide were consumed, producing an alkanol ethoxylate having a mean average adduct number of 2.6.

EXAMPLE 18

In another alkoxylation process embodiment according to the invention, 3.0 grams (0.008 mols) of LaCl was dissolved in 200 grams of NEODOL 23 Alcohol and nitrogen sparged for 3 hours at 130° C. The resulting mixture was transferred to the autoclave reactor and reacted with ethylene oxide at 170° C. for 6 hours. A total of 10 grams of ethylene oxide was consumed during this period.

EXAMPLE 19

In another alkoxylation process embodiment according to the invention, 3.0 grams (0.007 moles) of La(NO$_3$)$_3$.6H$_2$O was dissolved in 200 grams of NEODOL 23 Alcohol and nitrogen sparged for 3 hours at 130° C. The resulting mixture was transferred to the autoclave reactor and reacted with ethylene oxide at 170° C. for 3.5 hours. A total of 40 grams of ethylene oxide was consumed during this period.

EXAMPLE 20

A catalyst was prepared according to the following procedure. A total of 10.9 grams of Ce(NO$_3$)$_3$.6H$_2$O was dissolved in 100 grams of deionized water and this solution was heated to 60° C. A solution formed by dissolving 3 grams of 85% w H$_3$PO$_4$ in 10 grams of deionized water was added to the aqueous cerium nitrate solution. The total solution was stirred for an additional hour at 80° C. The resulting mixture, which contained a fine white solid, was cooled to 25° C., and the solid was isolated and washed free of any residual acid. After drying under vacuum at 50° C., a total of 5.8 grams of a free flowing, off-white powder was obtained.

One gram of this powder was added to 195 grams of the NEODOL 23 Alcohol, and the mixture was heated to 130° C. under nitrogen sparge for 2 hours to drive off water. The resulting mixture was transferred to an autoclave reactor and the alcohol ethoxylated at 140° C. and at a pressure of psia (30 psia ethylene oxide and 50 psia nitrogen). A total of 309 grams of ethylene oxide was consumed over a period of 2 hours, yielding a product having a mean average adduct number of 6.8. The adduct distribution of this product is presented in the following table.

| ETHOXYLATE DISTRIBUTION | |
|---|---|
| Adduct Number | Concentration |
| 0 (Residual Alcohol) | 1.4% w |
| 1 | 0.5 |
| 2 | 0.6 |
| 3 | 1.0 |
| 4 | 2.7 |
| 5 | 8.5 |
| 6 | 18.4 |
| 7 | 24.4 |
| 8 | 20.3 |
| 9 | 11.9 |
| 10 | 5.6 |
| 11 | 2.5 |
| 12 | 1.2 |
| 13 | 0.6 |
| 14 | 0.4 |
| 15 | 0.2 |

EXMAPLE 21

A catalyst was prepared under the following procedure. A total of 0.99 gram of 85% w H$_3$PO$_4$ dissolved in 14 grams of deionized water was added to a suspension of 8.5 grams of praseodymium oxide (Pr$_6$O$_{11}$) in 140 grams of deionized water, heated to 60° C. The resulting mixture was stirred for an additional hour at 80° C. A solid product formed and was isolated by filtration and washed several times with deionized water until the washings were neutral to pH paper. The reddish-brown solid was dried in vacuo at 80° C. producing 8.8 grams of a fine, free-flowing powder.

Three grams of this powder was added to 200 grams of NEODOL 23 Alcohol. An ethoxylation reaction was then carried out according to the procedures described in Example 20. A total of 318 grams of ethylene oxide was consumed over a 2 hour period at a reaction temperature of 155° C. The product had a mean average adduct number of 6.6. The adduct distribution of this product is presented in the following table.

| ETHOXYLATE DISTRIBUTION | |
|---|---|
| Adduct Number | Concentration |
| 0 (Residual Alcohol) | 2.0% w |
| 1 | 0.6 |
| 2 | 0.6 |
| 3 | 1.3 |
| 4 | 3.7 |
| 5 | 10.1 |
| 6 | 18.6 |
| 7 | 21.4 |
| 8 | 17.0 |
| 9 | 10.5 |
| 10 | 8.8 |
| 11 | 3.2 |
| 12 | 1.8 |
| 13 | 1.1 |
| 14 | 0.8 |
| 15 | 0.5 |
| 16 | 0.4 |
| 17 | 0.3 |
| 18 | 0.2 |

EXAMPLE 22

A catalyst was prepared according to the procedures described in i Example 21, except that 5.94 grams of 85% w $H_3PO_4$ was used instead of 0.99 L gram. (This represented a molar ratio of $H_3PO_4$ to $Pr_6O_{11}$ of 6:1 instead of 1:1 as in Example 21.) The catalyst was isolated in the same manner and used directly in ethoxylation. Three grams of the catalyst was added to grams of NEODOL 23 Alcohol and the alcohol was ethoxylated under the conditions described in Example 20. A total of 312 grams of ethylene oxide was consumed over a 3 hour period. The average adduct number of the product was 6.9. The adduct distribution of the product is presented in the following table.

| ETHOXYLATE DISTRIBUTION | |
|---|---|
| Adduct Number | Concentration |
| 0 (Residual Alcohol) | 1.3% w |
| 1 | 0.5 |
| 2 | 0.5 |
| 3 | 0.9 |
| 4 | 2.4 |
| 5 | 7.2 |
| 6 | 16.5 |
| 7 | 23.5 |
| 8 | 22.1 |
| 9 | 13.9 |
| 10 | 6.7 |
| 11 | 2.7 |
| 12 | 1.1 |
| 13 | 0.5 |
| 14 | 0.2 |
| 15 | 0.1 |

EXAMPLE 23

A catalyst was prepared according to the general procedures of Example 21 using a rare earth mixture obtained from the Molycorp Corporation. The mixture was a rare earth hydroxy chloride having a distribution of rare earth metals: 15% w Ce, 57% w La, 20% w Nd and 8% w Pr, each in the form of its hydroxy chloride salt. A solution of 3 grams of 85% w $H_3PO_4$ in 14 grams of deionized water was added to a suspension of 5.2 grams of the rare earth hydroxy chloride mixture in 140 grams of deionized water heated to 60° C. The catalyst was prepared as described following the general procedures of Example 21 and isolated by centrifugation. The recovered solid was washed several times with deionized water to remove traces of residual phosphoric acid. The solid was dried in vacuo at 80° C., and a total of 6.15 grams was isolated as a free flowing, off-white powder.

One gram of this powder was added to 195 grams of NEODOL 23 Alcohol, and the mixture was then dried at 130° C. under nitrogen sparge to remove water. The alcohol was ethoxylated under the same procedures as described in Example 20. A total of 310 grams ethylene oxide was consumed over 80 minutes. The product was determined to have an average adduct number of 7.0. The adduct distribution of the product is presented in the following table.

| ETHOXYLATE DISTRIBUTION | |
|---|---|
| Adduct Number | Concentration |
| 0 (Residual Alcohol) | 1.4% w |
| 1 | 0.5 |
| 2 | 0.4 |
| 3 | 0.9 |
| 4 | 2.4 |
| 5 | 7.5 |
| 6 | 17.0 |
| 7 | 22.3 |
| 8 | 21.2 |
| 9 | 12.9 |
| 10 | 6.7 |
| 11 | 3.1 |
| 12 | 1.9 |
| 13 | 0.8 |
| 14 | 0.5 |
| 15 | 0.3 |
| 16 | 0.2 |
| 17 | 0.1 |

EXAMPLE 24

A catalyst was prepared according to the following procedure. A total of 2.0 grams of neodymium isopropoxide was dissolved in 50 grams of 2-ethoxyethanol and 200 grams of NEODOL 23 Alcohol. The mixture was heated to 70° C. at which time 0.668 gram of 96% w $H_2SO_4$ was added dropwise over approximately 3 minutes. The resulting mixture was stirred at 70° C. for an additional 30 minutes, after which the 2-ethoxyethanol and isopropanol (produced from transalcoholysis with NEODOL 23 Alcohol) was removed via vacuum distillation. The resulting 201 grams of mixture containing the catalyst was transferred to the autoclave reactor and the alcohol ethoxylated according to the general procedures described in Example 20. A total of 192 grams of ethylene oxide was consumed over a 10 hour period at a 170° C. reaction temperature. The product obtained was found to have an average adduct number of 2.9. The adduct distribution is presented in the following table.

| ETHOXYLATE DISTRIBUTION | |
|---|---|
| Adduct Number | Concentration |
| 0 (Residual Alcohol) | 6.7% w |
| 1 | 18.3 |
| 2 | 16.6 |
| 3 | 13.8 |
| 4 | 11.6 |
| 5 | 9.6 |
| 6 | 7.4 |
| 7 | 3.8 |
| 8 | 3.4 |
| 9 | 2.7 |
| 10 | 2.0 |
| 11 | 1.5 |
| 12 | 1.2 |
| 13 | 0.9 |
| 14 | 0.7 |

EXAMPLE 25

A catalyst was prepared according to the procedures described in Example 24 using 2 grams of cerium isopropoxide and 0.65gram of 96% w $H_2SO_4$. A total of 194 grams of the mixture containing the catalyst in NEODO1 23 Alcohol was transferred to the autoclave and the alcohol ethoxylated as described in Example 24. A total of 109 grams of ethylene oxide was added and consumed over 4 hours. The average adduct number of the product was 1.6. The adduct distribution is presented in the following table.

| ETHOXYLATE DISTRIBUTION | |
|---|---|
| Adduct Number | Concentration |
| 0 (Residual Alcohol) | 18.6% w |
| 1 | 30.1 |
| 2 | 20.9 |
| 3 | 13.9 |
| 4 | 8.7 |
| 5 | 4.8 |
| 6 | 2.5 |
| 7 | 0.4 |

EXAMPLE 16

A slurry of 5.00 grams samarium oxide with 110 grams of NEODO1 23 Alcohol in a 500 ml autoclave was contacted with ethylene oxide at a pressure of 100 psia (60 psia nitrogen, 40 psia ethylene oxide) and a temperature of 120° C. A total of 35 grams of ethylene oxide was consumed over 3.5 hours. Analysis by gas chromatography indicated formation of alcohol ethoxylate.

EXAMPLE 27

A slurry of 2.50 grams of ytterbium oxide with 110 grams of NEODOL 23 Alcohol in a 500 ml autoclave was contacted with ethylene oxide at a pressure of 100 psia (60 psia nitrogen and 40 psia ethylene oxide) and a temperature of 120° C. A total of 22 grams of ethylene oxide was consumed over 1.5 hours. Alcohol ethoxylate formation was confirmed by gas chromatography.

I claim as my invention:

1. A process for the preparation of alkylene oxide adducts of active hydrogen containing organic compounds, which comprises contacting and reacting reactants consisting of (a) one or more alkylene oxides selected from the group consisting of ethylene oxide and propylene oxide and (b) one or more active hydrogen containing organic compounds, in the presence of a catalytically effective amount of one or more monometallic salts of one or more of the rare earth elements.

2. The process of claim 1, wherein the one or more active hydrogen containing compounds consist essentially of compounds selected from the group consisting of alcohols, phenols and polyols.

3. The process of claim 2, wherein the active hydrogen moiety of the one or more active hydrogen containing organic compounds is attached to a primary carbon atom.

4. The process of claim 3, wherein the active hydrogen containing compounds are selected from the group consisting of alkanols having from one to about 30 carbon atoms and alkyl-substituted phenols wherein each alkyl substituent has from one to about 30 carbon atoms.

5. The process of claim 4, wherein the active hydrogen containing compounds are $C_1$–$C_{30}$ primary mono-hYdric alkanols.

6. The process of claim 5, wherein the active hydrogen containing compounds consist essentially of primary mono-hydric alkanols having carbon numbers in the range from 6 to 24, inclusive, and the alkylene oxide is ethylene oxide.

7. The process of claim 6, wherein the active hydrogen containing compounds consist essentially of primary mono-hydric alkanols having carbon numbers in the range from 8 to 20, inclusive.

8. The process of claim 7, wherein greater than about 50% of the molecules of the primary mono-hydric alkanols are of linear carbon structure.

9. The process of claim 8, wherein greater than about 70% of the molecules are of linear carbon structure.

10. The process of any one of claims 3, 6, and 9, carried out in the presence of a catalytically effective amount of one or more alcoholate or phenolate compounds of one or more of the rare earth elements.

11. The process of claim 10, carried out in the presence of one or more alkoxide compounds.

12. The process of claim 11, wherein the alkoxide compounds have —OR substituents wherein R is an alkyl group in the $C_8$ to $C_{20}$ range.

13. The process of claim 12, wherein the alkoxide compounds have at least one —OR substituent corresponding to the alkanols in the active hydrogen containing reactant.

14. A process for the preparation of alkylene oxide adducts of active hydrogen containing organic compounds, which comprises contacting and reacting reactants consistiong of (a) one or more alkylene oxides selected from the group consisting of ethylene oxide and propylene oxide and (b) one or more active hydrogen containing organic compounds, in the presence of a catalytically effective amount of one or more monometallic salts of one or more elements selected from the group consisting of lanthanum, cerium, praseodymium, neodymium, samarium, gadolinium, dysprosoium, erbium, and ytterbium.

15. The process of claim 14, wherein the active hydrogen containing compounds consist essentially of compounds selected from the group consisting of alcohols, phenols and polyols.

16. The process of claim 15, wherein the active hydrogen moiety of the one or more active hydrogen containing compounds is attached to a primary carbon atom.

17. The process of claim 16, wherein the active hydrogen containing compounds consist essentially of compounds selected from the group consisting of alkanols having from one to about 30 carbon atoms and alkyl-substituted phenols wherein each alkyl substituent has from one to about 30 carbon atoms.

18. The process of claim 17, wherein the active hydrogen containing compounds consist essentially of $C_1$–$C_{30}$ primary mono-hydric alkanols.

19. The process of claim 18, wherein the active hydrogen containing compounds consist essentially of primary mono-hydric alkanols having carbon numbers in the range from 6 to 24, inclusive, and the alkylene oxide reactant consists essentially of ethylene oxide.

20. The process of claim 19, wherein the active hydrogen containing compounds consist essentially of primary mono-hydric alkanols having carbon numbers in the range from 8 to 20, inclusive.

21. The process of claim 20, wherein greater than about 50% of the molecules of the primary mono-hydric alkanols are of linear carbon structure.

22. The process of claim 21, wherein greater than about 70% of the molecules are of linear carbon structure.

23. The process of any one of claims 16, 19 and 22, carried out in the presence of a catalytically effective amount of one or more alcoholate or phenolate compounds of one or more of the rare earth elements.

24. The process of claim 23, carried out in the presence of one or more alkoxide compounds.

25. The process of claim 24, wherein the alkoxide compounds have —OR substituents wherein R is an alkyl group in the $C_8$ to $C_{20}$ range.

26. The process of claim 25, wherein the alkoxide compounds have at least one —OR substituent corresponding to the alkanols in the active hydrogen containing reactant.

27. The process of claim 1, wherein the one or more alKylene oxides are contacted and reacted with the one or more active hydrogen containing compounds in the presence of a catalytically effective amount of one or more mono-metallic salts of the rare earth element yttrium.

28. The process of claim 1, wherein the one or more alkylene oxides are contacted and reacted with the one or more active hydrogen containing compounds in the presence of a catalytically effective amount of one or more mono-metallic salts of the rare earth element cerium.

29. The process of claim 1, wherein the one or more alkylene oxides are contacted and reacted with the one or more active hydrogen containing compounds in the presence of a catalytically effective amount of one or more mono-metallic salts of the rare earth element praseodymium.

30. The process of claim 1, wherein the one or more alkylene oxides are contacted and reacted with the one or more active hydrogen containing compounds in the presence of a catalytically effective amount of one or more mono-metallic salts of the rare earth element neodymium.

31. The process of claim 1, wherein the one or more alkylene oxides are contacted and reacted with the one or more active hydrogen containing compounds in the presence of a catalytically effective amount of one or more mono-metallic salts of the rare earth element samarium.

32. The process of claim 1, wherein the one or more alkylene oxides are contacted and reacted with the one or more active hydrogen containing compounds in the presence of a catalytically effective amount of one or more mono-metallic salts of the rare earth element gadolinium.

33. The process of claim 1, wherein the one or more alkylene oxides are contacted and reacted with the one or more active hydrogen containing compounds in the presence of a catalytically effective amount of one or more mono-metallic salts of the rare earth element lanthanum.

34. The process of claim 1, wherein the one or more alkylene oxides are contacted and reacted with the one or more active hydrogen containing compounds in the presence of a catalytically effective amount of one or more mono-metallic salts of the rare earth element dysprosium.

35. The process of claim 1, wherein the one or more alkylene oxides are contacted and reacted with the one or more active hydrogen containing compounds in the presence of a catalytically effective amount of one or more mono-metallic salts of the rare earth element erbium.

36. The process of claim 1, wherein the one or more alkylene oxides are contacted and reacted with the one or more active hydrogen containing compounds in the presence of a catalytically effective amount of one or more mono-metallic salts of the rare earth element ytterbium.

37. The process of any of claims 27, 28, 29, 30, 31, 32, 33, 34 35, and 36, wherein the active hydrogen containing compounds consist essentially of one or more compounds selected from the group consisting of alcohols, phenols and polyols having an active hydrogen moiety attached to a primary carbon atom.

38. The process of claim 37, wherein the active hydrogen containing compounds consist essentially of primary mono-hydric alkanols having carbon numbers in the range from 6 to 24, inclusive, and the alKylene oxide reactant is ethylene oxide.

39. The process of claim 38, wherein the active hydrogen containing compounds consist essentially of primary mono-hydric alkanols having carbon numbers in the range from 8 to 20, inclusive, wherein greater than about 70% of the primary mono-hydric alkanol molecules are of linear carbon structure.

40. The process of claim 37, wherein the active hydrogencontaining compounds consist essentially of polyols having from 2 to about 6 hydroxyl groups and the alkylene oxide reactant is propylene oxide.

41. The process of claim 1, wherein the simple metal salts are organic salts.

42. The process of claim 1, wherein the simple metal salts are inorganic salts.

43. The process of either of claims 41 and 42, wherein the alkylene oxide reactant is ethylene oxide.

44. The process of claim 43, wherein the active hydrogencontaining reactant consists essentially of one or more primary monohydric alkanols having carbon numbers in the range from 8 to 20, inclusive.

45. The process of either of claims 41 and 42, wherein the active hydrogen-containing compounds consist essentially of polyols having from 2 to about 6 hydroxyl groups.

46. A process for the preparation of alkylene oxide adducts of active hydrogen containing organic compounds, which comprises contacting and reacting reactants consistiong of (a) one or more alkylene oxides selected from the group consisting of ethylene oxide and propylene oxide and (b) one or more active hydrogen containing organic compounds, in the presence of a catalytically effective amount of a mixture of mono-metallic salts, said mixture containing salts of at least two different elements selected from the group consisting of yttrium, lanthanum, cerium, praseodymium, neodymium, samarium, gadolinium, dysprosoium, erbium, and ytterbium.

47. The process of claim 46, carried out in the presence of a catalytically effective amount of one or more mono-metallic salts of a mixture of rare earth elements selected from the group consisting of bastnasite, monazite, xenotime, didymium, gadolinite and euxenite.

48. The process of claim 47, wherein the mono-metallic salts are organic salts.

49. The process of claim 47, wherein the mono-metallic salts are inorganic salts.

50. The process of either of claims 48 and 49, wherein the alkylene oxide reactant is ethylene oxide.

51. The process of claim 50, wherein the active hydrogencontaining compounds consist essentially of one or more primary monohydric alkanols having carbon numbers in the range from 8 to 20, inclusive.

52. The process of either of claims 48 and 49, wherein the active hydrogen-containing compounds consist essentially of polyols having from 2 to about 6 hydroxyl groups.

53. A process for the preparation of ethylene oxide adducts of higher alkanols, which comprises contacting and reacting reactants consisting of (a) ethylene oxide and (b) one or more $C_8$ to $C_{20}$ primary mono-hydric alkanols in the presence of a catalytically effective amount of one or more mono-metallic salts of one or more of the elements of the lanthanum series.

54. The process of claim 53, wherein greater than about 50% of the alkanol molecules are of linear carbon structure.

55. The process of claim 54, carried out in the presence of a catalytically effective amount of one or more mono-metallic salts of one or more of the elements selected from the group consisting of lanthanum, cerium, neodymium, and praseodymium.

56. A process for the preparation of alkylene oxide adducts of active hydrogen containing organic compounds, which comprises contacting and reacting reactants consisting of (a) one or more alkylene oxides selected from the group consisting of ethylene oxide and propylene oxide and (b) one or more active hydrogen containing organic compounds, in the presence of a catalytically effective amount of one or more rare earth metals.

57. A process for the preparation of ethylene oxide adducts of higher alkanols, which comprises contacting and reacting ethylene oxide with one or more $C_8$ to $C_{20}$ primary mono-hydrid alkanols in the presence of a catalytically effective amount of one or more mono-metallic salts of one or more of the elements selected from the group consisting of lanthanum, neodymium, and praseodymium.

58. The process of claim 57, wherein greater than about 50% of the alkanol molecules are of linear carbon structure.

* * * * *